United States Patent [19]

Arpe

[11] 4,169,959

[45] Oct. 2, 1979

[54] PROCESS FOR THE PREPARATION OF ETHYLENE GLYCOL-DIMETHYLETHER (DIMETHYL GLYCOL)

[75] Inventor: Hans-Jürgen Arpe, Kelkheim, Fed. Rep. of Germany

[73] Assignee: Hoechst Aktiengesellschaft, Frankfurt, Fed. Rep. of Germany

[21] Appl. No.: 896,231

[22] Filed: Apr. 13, 1978

[30] Foreign Application Priority Data

Apr. 15, 1977 [DE] Fed. Rep. of Germany ....... 2716690

[51] Int. Cl.$^2$ ............................................. C07C 41/00
[52] U.S. Cl. .................................... 568/672; 568/678; 568/613
[58] Field of Search .................... 260/615 R; 568/672, 568/613, 678

[56] References Cited

U.S. PATENT DOCUMENTS

| 2,397,514 | 4/1946 | Staff | 260/615 R |
| 3,170,958 | 2/1965 | Howard | 260/615 R |
| 3,972,949 | 8/1976 | Arpe | 260/615 R |

*Primary Examiner*—Howard T. Mars
*Attorney, Agent, or Firm*—Curtis, Morris & Safford

[57] ABSTRACT

A process for the preparation of dimethyl glycol by the hydrogenolysis of methylglycol formal in the presence of catalysts which consist of oxide mixtures of silicon and aluminum and/or of rare earths, as well as of metallic nickel and/or cobalt and/or copper, wherein the catalysts contain additionally as promoter metallic palladium and/or rhodium and/or platinum.

3 Claims, No Drawings

PROCESS FOR THE PREPARATION OF ETHYLENE GLYCOL-DIMETHYLETHER (DIMETHYL GLYCOL)

The present invention relates to a process for the preparation of ethylene glycol-dimethylether (dimethyl glycol).

It has already been proposed to prepare ethylene glycol-dimethylether of the general formula $CH_3O(CH_2CH_2O)_nCH_3$ with n being a number of from 1 to 8, which is usually called dimethyl-glycol ether, from the formals of the corresponding glycol-monomethyl ethers by way of hydrogenolysis in the presence of catalysts which consist of oxide mixtures of silicon and of aluminum and/or of rare earths and which contain additionally the metals of nickel and/or cobalt and/or copper (German Offenlegungsschrift No. 2 434 057).

The catalysts possess a very high initial activity with regard to the conversion of the formal of the monomethylglycol ethers and a very high selectivity with regard to the formation of the dimethyl-glycol ethers. When being used in discontinuous hydrogenolysis tests in the autoclave, the catalysts initially display sufficient stability of their activity. However, they can only be successively used several times with the desired high, and thus economical, hydrogenation activity in those cases where the continuous decrease of the formalconversion is compensated by a slight increase of the reaction temperature. Such an increase of the reaction temperature is generally acceptable only to a limited extent, since this promotes side and secondary reactions and may thus lead to a decrease in selectivity. On the other hand, if the hydrogenolysis temperature is maintained constant, a decrease of the activity to about 50% of the initial value is realized, after the catalyst has been repeatedly used about ten times.

Surprisingly, it has now been found that the decrease in activity of the above-mentioned catalysts can be avoided by the addition of promoter metals, such as rhodium and/or palladium and/or platinum, i.e. the catalyst activity can be stabilized at a high value. The stabilization is most desirable for those catalysts which are to be used for the hydrogenolysis of the formal of glycol-monomethyl ether $(CH_3OCH_2CH_2O)_2CH_2$—hereinafter simply termed methylglycol formal—i.e. for the preparation of dimethyl glycol $CH_3OCH_2CH_2OCH_3$, since the addition of the promoter metal has no influence on the selectively hydrogenating cleavage of the methylglycol formal in this case.

The process of the invention for the preparation of dimethyl glycol by the hydrogenolysis of methylglycol formal in the presence of catalysts consisting of oxide mixtures of silicon and aluminum and/or of rare earths, as well as metallic nickel and/or cobalt and/or copper requires that the catalysts contain additionally metallic palladium and/or rhodium and/or platinum as promoters.

Thus, the promoters are the elements Pd, Rh and Pt individually, the double combinations Pd/Rh, Pd/Pt, Rh/Pt as well as the triple combination Pd/Rh/Pt.

Besides dimethyl glycol there is always formed monomethyl glycol in an equimolar amount.

By the addition of the promoter the economy of the process for the preparation of dimethyl glycol, which is already favorable, is improved again to a considerable extent, since with a discontinuous process the hydrogenolysis catalyst may be used many times successively under the same conditions, without any decrease of its activity and selectivity. Moreover, the prolonged service life of the catalyst also makes a continuous operation possible which has additional technical advantages over the discontinuous method.

Fundamentally, two methods may be used for the preparation of the catalyst:

The first method consists of initially preparing the known catalyst which contains oxide mixtures of silicon and aluminum and/or of rare earths as well as metallic nickel and/or cobalt and/or copper, which catalyst is hereafter referred to as a basic catalyst. This basic catalyst is then impregnated with salts of rhodium and/or palladium and/or platinum and is subsequently reduced.

The second method consists in introducing the promoter metals as salts at a suitable stage during the preparation of the basic catalyst. It would be suitable, for example, to impregnate the basic catalyst with the promoters together with the salts of nickel, cobalt or copper. Another method is the joint precipitation of all catalyst components including the promoters as hydroxides, oxides or oxide hydrates by adjusting the pH value of an aqueous solution of appropriate salts with aqueous ammonia or alkali hydroxide solutions to a range of from about 7 to 8. The component mixture is then dried, reduced and calcined in this form, as described below. Modifications of this latter method of preparation are possible. Thus, for example, the components of the basic catalyst can be precipitated first as oxides or oxide hydrates, then they are washed until they are free from foreign ions and thereafter mixed in an aqueous suspension with salt solutions of the promoter metals. The surface of the oxides or oxide hydrates of the basic catalyst which is alkaline leads to the precipitation of the promoter metals in the form of their hydroxides, oxides or oxide hydrates. Then follows the drying at a temperature of from about 100° to 150° C., the reduction with gases having a reducing effect, such as hydrogen, CO or methanol vapors at a temperature of from 200° to 600° C., preferably from 300° to 500° C., and the calcination at a temperature of from 150° to 850° C., preferably from 500° to 700° C., for a period of from 1 to 30 hours, preferably from 3 to 20 hours. As suitable compounds of the promoter metals rhodium, palladium and platinum there are to be mentioned above all salts, as the nitrates, chlorides, acetates, or complex compounds, such as acetylacetonates. There are other suitable compounds like, for example, oxides, hydroxides or carbonates which are soluble in aqueous mineral acid or carboxylic acids. The weight ratio of the promoter metal to the metals nickel, cobalt or copper which are present in the basic catalyst may vary within a wide range of from about 0.01 to about 10% by weight. The preferred weight ratio is in the range of from 0.1 to 1% by weight.

The hydrogenolysis is effected in the process of the invention generally at a temperature of from 50° to 250° C. and at a hydrogen pressure of from 30 to 300 bars. But satisfactory activity and selectivity values may also be expected beyond these limits.

The hydrogenating cleavage of the methylglycol formal may be effected with pure hydrogen or with hydrogen that has been diluted with inert gases, such as $N_2$, $CH_4$ or $CO_2$. This process can be carried out discontinuously, for example in an autoclave with a finely divided agitated catalyst. However, the hydrogenating cleavage may also be effected in pressure reactors continuously, in the vapor or trickling phase or in the sump phase, at a catalyst which is usually fixed. But other known hydrogenation methods with a heterogeneous-catalyst are suitable as well. The formal can be used in a pure undiluted form, however, it may also be used for the reaction while being diluted with a solvent, for example with alcohols—such as methanol—or ethers, or with the reaction product, i.e. monomethyl glycol or dimethyl glycol.

After the calculated amount of hydrogen has been absorbed when using an autoclave or following the passage through a reactor together with hydrogen in parallel flow or in counter-current, the reaction products are separated by distillation. If the process is carried out without solvents or with the reaction products as solvents, the working-up of the reaction mixture can be effected in a particularly simple manner; dimethyl glycol is the product that has the lowest boiling point. It can be separated, for example, by fractional distillation or by a thin-film evaporation as the low boiling fraction. Unreacted formal and monomethyl glycol are again reacted in a known manner with a solution or substance yielding formaldehyde to give the methylglycol formal.

The factors used in the following Examples for the formal used and the mono- and dimethyl glycols formed from it are defined as follows:

The conversion of the formal is the ratio of the amount converted over the amount of normal feed.

The selectivity of monomethyl glycol or dimethyl glycol is the ratio of the amount formed of these ethers over the amount of formal converted.

The conversion and the selectivity have been indicated in mole percent.

Due to the stoichiometry of the following reaction equation I the selectivity with regard to monomethyl glycol as well as dimethyl glycol may be 100 mole percent in each case under optimum conditions. In the case of a non-selective cleavage of the formal, for example by formation of methane (reaction equation II), an overstoichiometric amount of monomethyl glycol can be formed, i.e. the selectivity can exceed 100%.

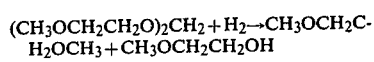

$$(CH_3OCH_2CH_2O)_2CH_2 + H_2 \rightarrow CH_3OCH_2CH_2OCH_3 + CH_3OCH_2CH_2OH \quad \text{I}$$

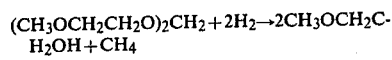

$$(CH_3OCH_2CH_2O)_2CH_2 + 2H_2 \rightarrow 2CH_3OCH_2CH_2OH + CH_4 \quad \text{II}$$

The following Examples serve to illustrate the invention.

COMPARISON EXAMPLE AND EXAMPLES 1 THROUGH 5

300 Grams of $Ni(NO_3)_2.6 H_2O$ and 74 g of $Al(NO_3)_3.9 H_2O$ are dissolved in 180 ml of $H_2O$ and mixed with 60 ml of a solution of the promoter metal salt specified in Table 1 below in concentrated nitric acid (about 69% by weight). Within 2 hours, this solution is introduced, while stirring, into a solution heated to a temperature of from 70° to 90° C. of 100 g of sodium silicate (about 25 to 30% by weight of $SiO_2$), and 120 g of $Na_2CO_3$ in 300 ml of water. The pH value of the mixture is adjusted to 8 with sodium hydroxide solution, and the suspension is stirred for 3 hours at a temperature in the range of from 70° to 90° C.

The precipitate is then filtered off with suction and is washed with water, until it is free from nitrate ions and—if promoter metal chlorides or -acetates are used—also free from chloride ions or acetate ions. After drying at 140° C. and at about 300 mbars, this preliminary catalyst is reduced for 9 hours at 400° C. with hydrogen and is subsequently calcined under a light hydrogen current for another 9 hours at 600° C.

For checking out the catalysts thus obtained for the hydrogenolysis of the methylglycol formal, less than optimal reaction conditions are chosen so as to obtain a relatively low conversion, in order to realize an improvement of the activity and selectivity as compared with a catalyst which does not contain any promoter metal. The comparison catalyst is prepared in a manner analogous to the one described above, but without any promoter addition. All catalysts are tested in the following manner:

200 Grams of methylglycol formal are subjected to hydrogenolysis in the presence of 2.5 g each of finely divided catalyst at a temperature of from 150° to 160° C. and from 65 to 70 bars of $H_2$ pressure in a 1 liter magnetic type lifting autoclave for one hour.

The reaction product is separated from the catalyst by filtration and is analyzed by way of gas chromatography. The results have been summarized in the following Table:

Table 1

| | Promoter metal salt | % by weight of promoter metal (calculated on Ni) | Conversion (in mole %) of methylglycol formal | Selectivities (mole %) | |
|---|---|---|---|---|---|
| | | | | mono-methyl glycol | di-methyl glycol |
| Comparison Example 1 | — | — | 45 | 82 | 115 |
| Example 1 | Pd acetate | 0.1 | 53 | 82 | 109 |
| 2 | " | 0.33 | 58 | 98 | 102 |
| 3 | " | 1.0 | 66 | 97 | 103 |
| 4 | Pt chloride | 1.0 | 71 | 87 | 113 |
| 5 | Rh chloride | 1.0 | 70 | 94 | 106 |

COMPARISON EXAMPLE 2

In 9 successive tests, 1.85 g each of methylglycol formal are hydrogenolyzed in a 5 liter magnetic type lifting autoclave in the presence of 3% by weight of a catalyst consisting of 60% by weight of nickel, 30% by weight of $SiO_2$ and 10% by weight of $Al_2O_3$, at a $H_2$ pressure of from 180 to 200 bars and a temperature of 200° C. The catalyst is prepared in the same manner as the catalyst in Comparison Example 1.

Upon completion of the hydrogen absorption, the catalyst is filtered off and is used again for the following test. In the course of this process it becomes evident that the conversion of formal of 98 molar percent in the first test of the catalyst decreases to 64 mole percent in the ninth test. The selectivity with regard to the glycol-dimethyl ether remains practically unaltered in the range of from 90 to 100 mole percent.

EXAMPLE 6

If in an analogous series of 9 successive tests, under conditions that are otherwise identical with those in Comparison Example 2, use is made of a catalyst having the composition of 60% by weight of nickel, 30% by weight of $SiO_2$ and 10% by weight of $Al_2O_3$ and containing additionally 1% by weight of palladium (calculated on the nickel content), the catalyst having been prepared in a manner analogous to that described in Example 3, the conversion of the formal remains unaltered at 100 mole percent, and the selectivity with regard to the glycoldimethyl ether is in the range of from 96 to 100 mole percent.

EXAMPLE 7

A steel reactor with a double casing having a total volume of 1250 ml is charged with 800 ml (720 g) of a pelleted $Ni-Pd/Al_2O_3.SiO_2$ catalyst (60% by weight of Ni+0.1% by weight of Pd—calculated on Ni—prepared in a manner analogous to that of Example 1). The hydrogen and the methylglycol formal are fed into the reactor from below. The level of the liquid phase in the reactor is established by way of an overflow pipe and is maintained at a constant height with an outlet valve. In a continuous test run for more than 1150 hours, a conversion of 93 mole percent with a selectivity of 97.5 mole percent with regard to dimethyl glycol and of 100 mole percent with regard to monomethyl glycol are obtained with a single catalyst charge at 200° C. and a $H_2$ pressure of 160 bars with a dosage of 800 g/h of methylglycol formal. Under these conditions the space-time yield was 543 g dimethyl glycol per liter of catalyst and hour. The distillation of the hydrogenolysis product is effected in a 50 l distilling vessel and a 4 meter column at normal pressure. Following minor forerunnings, dimethyl glycol is obtained as main run, which is formed in a form usual in commerce according to the values determined with regard to density, refraction number and boiling range. The tails consist of methyl glycol and unreacted formal, which are jointly re-used for the formal preparation.

I claim:

1. In a process for the preparation of dimethyl glycol by the hydrogenolysis of methylglycol formal in the presence of a catalyst which comprises a mixture of silicon dioxide and aluminum oxide and/or an oxide of a rare earth, and in addition metallic nickel, cobalt, copper or a combination thereof, the improvement which comprises carrying out said hydrogenolysis in the presence of said catalyst additionally containing metallic palladium, rhodium, platinum or a combination thereof as promoters.

2. Process as claimed in claim 1, wherein the weight ratio of the metallic promoter to the metals nickel, cobalt or copper is in the range of from 0.01 to 10%.

3. Process as claimed in claim 2, wherein the weight ratio is in the range of from 0.1 to 1%.

* * * * *